United States Patent [19]

Govang et al.

[11] Patent Number: 5,236,239
[45] Date of Patent: Aug. 17, 1993

[54] ADAPTER FOR A DEVICE USED TO PICK UP OBJECTS

[75] Inventors: Michael P. Govang, Billerica; Brian R. Finneral, Lowell, both of Mass.

[73] Assignee: Bruker Instruments, Inc., Billerica, Mass.

[21] Appl. No.: 673,145

[22] Filed: Mar. 21, 1991

[51] Int. Cl.⁵ .......................................... B25J 15/10
[52] U.S. Cl. .................................. 294/86.4; 294/88; 294/115; 294/116
[58] Field of Search ........ 294/1.1, 82.32, 86.29–86.32, 294/86.4, 87.22, 88, 95, 97, 100, 106, 113, 115, 116; 279/1 A, 1 F, 37, 38, 50, 51, 57, 58, 74; 901/31, 36–39

[56] References Cited

U.S. PATENT DOCUMENTS

| 4,017,112 | 4/1977 | Delest ............................ 294/82.32 |
| 4,091,323 | 5/1978 | Landis . |
| 4,199,183 | 4/1980 | Hecker ................................ 294/97 |
| 4,234,223 | 11/1980 | O'Neil ............................ 294/116 X |
| 4,581,583 | 4/1986 | Van Vliet et al. . |
| 4,629,237 | 12/1986 | Ito ........................................ 294/88 |
| 4,654,592 | 3/1987 | Zens . |
| 4,660,877 | 4/1987 | Schmidt et al. ................. 294/115 X |
| 4,705,311 | 11/1987 | Regard ............................ 294/88 X |
| 4,859,948 | 8/1989 | Kuster . |
| 4,892,344 | 1/1990 | Takada et al. ........................ 294/88 |
| 4,924,738 | 5/1990 | Che .................................. 294/115 X |

FOREIGN PATENT DOCUMENTS

| 38678 | 9/1985 | Japan ..................................... 294/95 |
| 62-63846 | 3/1987 | Japan . |
| 630193 | 11/1978 | U.S.S.R. ............................... 294/95 |
| 966644 | 8/1964 | United Kingdom .................. 294/88 |
| WO89/11646 | 11/1989 | World Int. Prop. O. . |

OTHER PUBLICATIONS

Bruker Instruments, Inc. *B.BPS: A totally new concept in routine NMR automation* (no date).
Bruker Analytische Messtechnik GBMH *200-250-300 MHz NMR Spectrometer: High-performance NMR Spectrometer for routine and research: AC.P* (no date).

Primary Examiner—Johnny D. Cherry
Attorney, Agent, or Firm—Cesari and McKenna

[57] ABSTRACT

An adapter is provided for a device which is used to pick up and transport objects. The device has a number of fingers which extend from a hollow piston. The adapter has an engaging portion which is inserted into the piston; a stopping piece for preventing the engaging piece from being inserted too far into the piston; and a receiving piece which has a cavity for receiving an object. The receiving piece and stopping piece each have openings which allow the fingers to pass through and grip the object while in the cavity.

12 Claims, 5 Drawing Sheets

ADAPTER FOR A DEVICE USED TO PICK UP OBJECTS

FIELD OF THE INVENTION

The present invention relates to devices for handling of materials, such as devices for transport of samples to and from a tester for those samples.

BACKGROUND OF THE INVENTION

In the field of materials testing, it has been a general practice to employ automated devices for acquisition of a liquid sample to be tested, transport of that sample to a testing apparatus, retrieval of the tested sample from the testing apparatus, and finally return of the sample whence it came or else provision of the tested sample to appropriate disposal. Often, such devices, particularly owing to their automatic nature, are designed or adapted to engage, transport and release samples of a predetermined size. However, there can be a need to have such specialized material handling apparatus also handle samples or containers of a different (e.g. smaller) size for which it was not designed. For example, this can occur when the testing device, for which the handling apparatus transports samples, is to be used for a different kind of sample than that for which the handling apparatus had been designed, intended or expected to use. For such situations, it is highly desirable to be able to adapt the handling apparatus to also handle such other samples, rather than replace that handling apparatus with another one. Replacement, instead of adaptation, would necessarily involve additional expense for the additional handling apparatus, as well as delay and expense in disassembling or deactivating the existing handling apparatus in order to install or activate the additional handling apparatus. This problem is overcome by the present invention.

One example of a prior art testing device and a prior art material handling apparatus is shown in FIG. 1. FIG. 1 shows a magnet chamber 13 of a nuclear magnetic resonance (NMR) spectrometer. Samples of liquid material are tested by the NMR spectrometer in magnet chamber 13. Such liquid samples are inserted in and removed from chamber 13 via room temperature shim assembly 15. Provision of samples of liquid material to assembly 15 and removal of those liquid samples therefrom is accomplished by material handling apparatus 17. Apparatus 17 includes a vertical cylinder 19 and piston 21 mounted on a rotatable arm 23. The lower end of piston 21 is provided with a pincher 37 for engaging and carrying a liquid sample. Arm 23 is rotatably supported on motorized pole 25 by upper and lower fixture rings 27 and 29 each connected to arm 23, and by resting ring 31 on which lower fixture ring 29 rests. Pole 25 is also provided with a pipe or tube 33 which supports magazine belt 35. Magazine belt 35 is configured to hold a plurality of liquid samples, and is rotated with rotation of pipe 33 so that different samples can be presented at different times to pincher 37. Cabinet 39 provides controls for movement of pipe 33 and pole 25. Pincher 37 with cylinder 19 and piston 21 can be moved horizontally or radially along arm 23, and may be moved azimuthally by swinging of arm 23 by rotation of pole 25 caused by cabinet 39. Pincher 37 is connected to the lower end of piston 21, and can be controlled to open and close about a liquid sample at belt 35 and cylinder 15. Cylinder 19, piston 21, arm 23 and pole 25 can thereby move pincher 37 between belt 35 and assembly 15.

Pincher 37 is shown in greater detail in FIG. 2 in a different stage of operation from that of FIG. 1. Fingers 41 can be furthermore extended further apart beyond the position of FIG. 2 so that liquid container 45 can be inserted therebetween. Pincher 37 includes a plurality (for example, five) of angled claw members or fingers 41 with a rigid collar 43. Fingers 41 are spring loaded to tend to stay together by an O-ring (not shown) disposed under collar 43. Although cylinder 19, piston 21 and fingers 41 are pneumatically activated, nonetheless hydraulic and/or electrical activation or control can alternatively be accomplished. Fingers 41, and especially slidable inner piston 42 to which the fingers are connected, move down and up, or out and in, as the fingers extend or retract, respectively. Fingers 41 can thereby be extended and retracted between their respective positions of FIGS. 1 and 2, or even beyond the latter position.

The lower portion of piston 21 is hollow, and is provided with a pneumatically (or otherwise) actuated and controlled slidable hollow cylindrical inner piston 42 coaxially and slidably disposed within the hollow portion of piston 21. Inner piston 42 has a cylindrical hollow 44 therein. Hollow 44 is open at the end of piston 42 at which fingers 41 are disposed. Fingers 41 are pivotably connected near the lower end of inner piston 42. As inner piston 42 moves downwardly in piston 21, the bends 46 of fingers 41 are moved free of collar 43, permitting the fingers to spread apart. Conversely, as inner piston 42 is withdrawn into or moved upwardly in piston 21, if fingers 41 had already been spread open, then the inner surface of collar 43 engages the bends 46 of those fingers, thereby drawing the fingers together. Since the liquid sample containers are generally made of glass, and so are frangible, it is necessary to control fingers 41 to grasp such containers firmly but gently.

The prior art apparatus of FIGS. 1 and 2 is designed for handling and testing of liquid samples such as are contained in liquid sample container 45 of FIG. 2. However, solid samples are disposed in holders or rotors 51 which are several times smaller than liquid containers 45. In particular, as shown in FIG. 2A, solid samples are disposed in rotor 51. Rotor 51 includes cap 47 and tube 49. Cap 47 is tightly press fitted on tube 49 whose opposite end is closed. Inside chamber 13, the toothed or ratcheted edges of cap 47 are engaged by compressed air to rotate the sample in a technique known in the art as "magic angle" spinning. For this reason, cap 47 and tube 49 are together known as a rotor 51.

A device such as that shown in FIGS. 1 and 2 is for example available from Bruker Instruments, Inc., Billerica, Mass. Alternatively, the samples and their containers or holders can be mounted on a moving carousel or turbine which is not mounted on pole 25.

Since rotor 51 is considerably smaller than the liquid containers 45 which pincher 37 is designed to engage, problems have been encountered in attempting to utilize pincher 37 to grip and carry rotor 51. Also, because of its larger size, container 45 can be raised out of assembly 15 by a cushion of air and supported thereby until engaged and transported away by pincher 37. However, because chamber 13 must be reconfigured to accommodate and utilize rotor 51, the rotor is ejected from magnet chamber 13 by a blast of compressed air. As can be seen in FIG. 2, piston 21, inner piston 42 and collar 43 are each hollow in the general vicinity of fingers 41.

Even if pincher 37 is appropriately positioned above assembly 15 with fingers 41 opened when such ejection occurs, it is difficult, if not impossible, to have fingers 41 close on rotor 51 in time. Rotor 51 can then be carried by the ejecting blast of air up into piston 21, which can cause damage to and/or loss of the sample. Furthermore, if pincher 37 is maneuvered by the rest of apparatus 17 while fingers 41 are fully extended, then those fingers can catch on and damage other portions of the apparatus of FIG. 1, and/or damage other apparatus, during movement of pincher 37.

SUMMARY OF THE INVENTION

Accordingly, it is the general purpose of the present invention to provide an adapter for a material handling apparatus that enables such apparatus to handle items differently sized from those which that apparatus was intended to handle.

Other objects of the present invention are to provide an adapter capable of reducing damage to and loss of such differently sized samples.

Further objects of the present invention are to provide an adapter capable of restricting extension or spreading of small pieces of that material handling apparatus to avoid damage to such apparatus and to other apparatus during movement of such pieces.

Still further objects of the present invention are to provide an adapter which enables such material handling apparatus to reliably grasp the differently sized sample holders or other items.

Briefly, these and other objects of the present invention are accomplished by an adapter including a first portion configured to be releasably retained within the engaging mechanism of a material handling apparatus, a stopping portion configured to prevent the adapter from traveling too far up into that engaging mechanism, and a receptacle or catching portion that is configured to guide and receive a moving material sample. The catching portion is provided with a plurality of openings, and the first and stopping portions are provided with a plurality of grooves, to accommodate portions of the engaging mechanism that are to engage such sample. Restraining means is also preferably provided on the catching portion to limit spreading of those portions of the engaging mechanism and thereby reduce damage to structure thereabout.

Other objects, advantages and novel features of the invention will become apparent from the following detailed description of the invention when considered in conjunction with the accompanying drawings.

DESCRIPTION OF THE PREFERRED EMBODIMENTS

Figure 1:
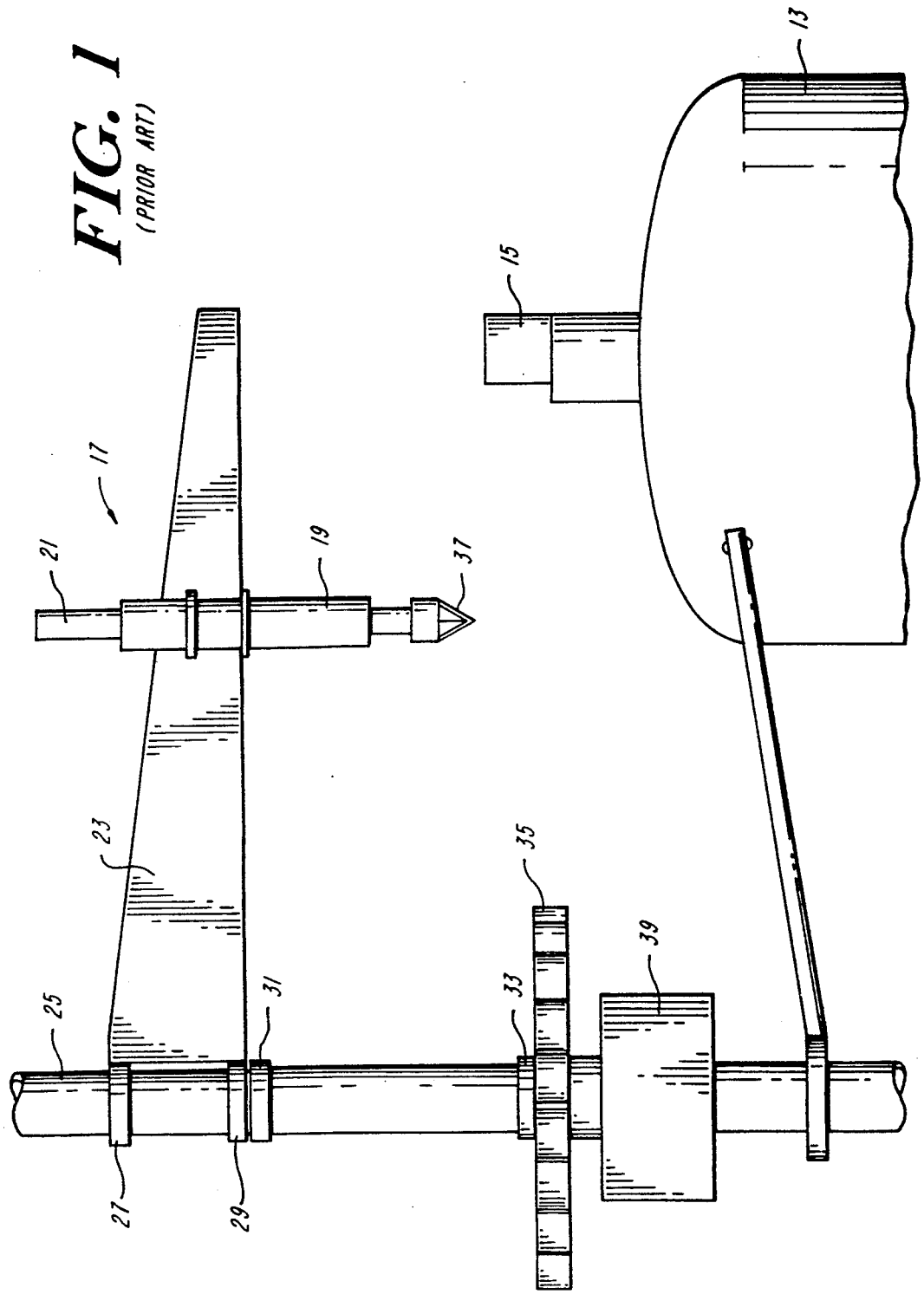
FIG. 1 shows a side elevation of a prior art material handling and testing apparatus in which the present invention can be utilized.
Figure 2:
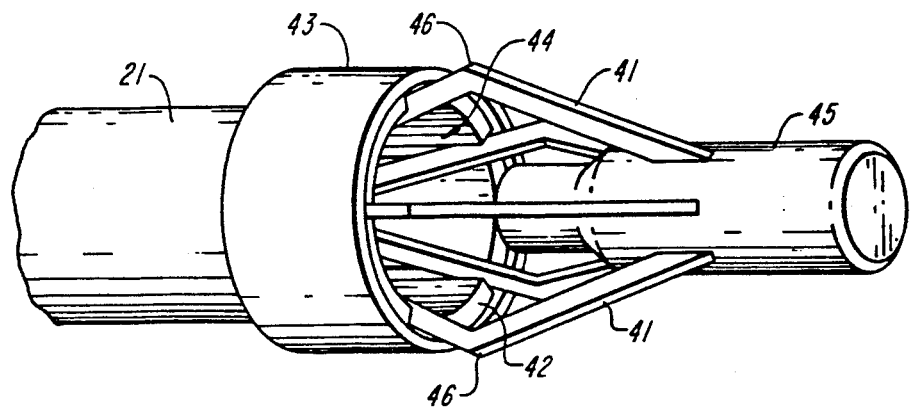
FIG. 2 is an enlarged view of a portion of the apparatus of FIG. 1 furthermore shown in operation engaging a prior art material container.
Figure 2A:
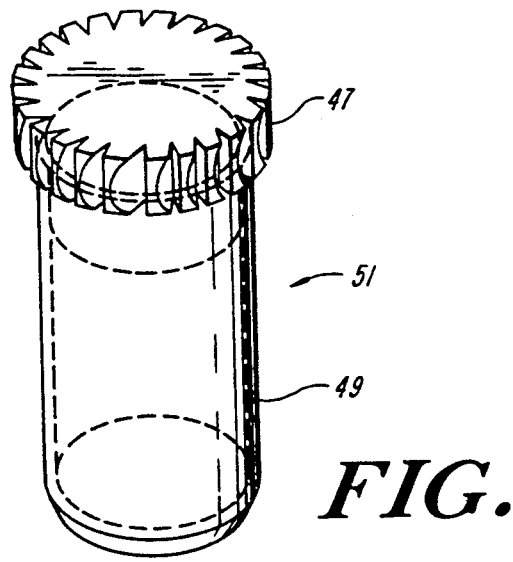
FIG. 2A illustrates a prior art holder for material samples to be tested, for which the apparatus of FIGS. 3-9 is particularly well suited.
Figure 3:
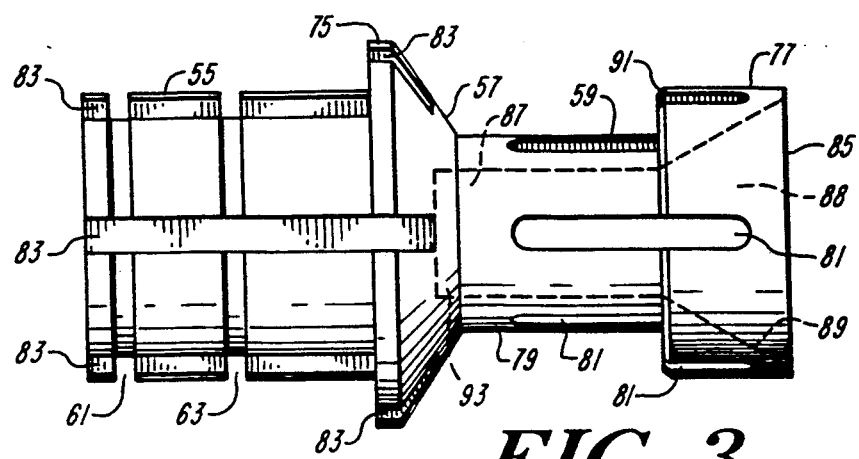
FIG. 3 shows a side elevation an embodiment of an adapter according to the present invention.
Figure 4:
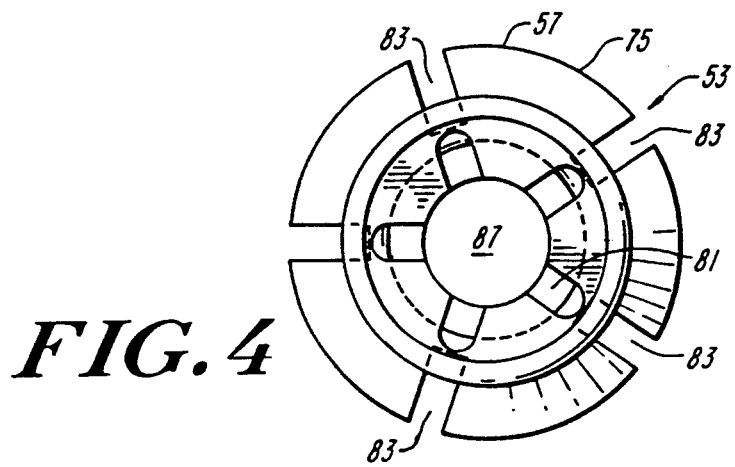
FIG. 4 shows an end view of the adapter of FIG. 3.
Figure 5:
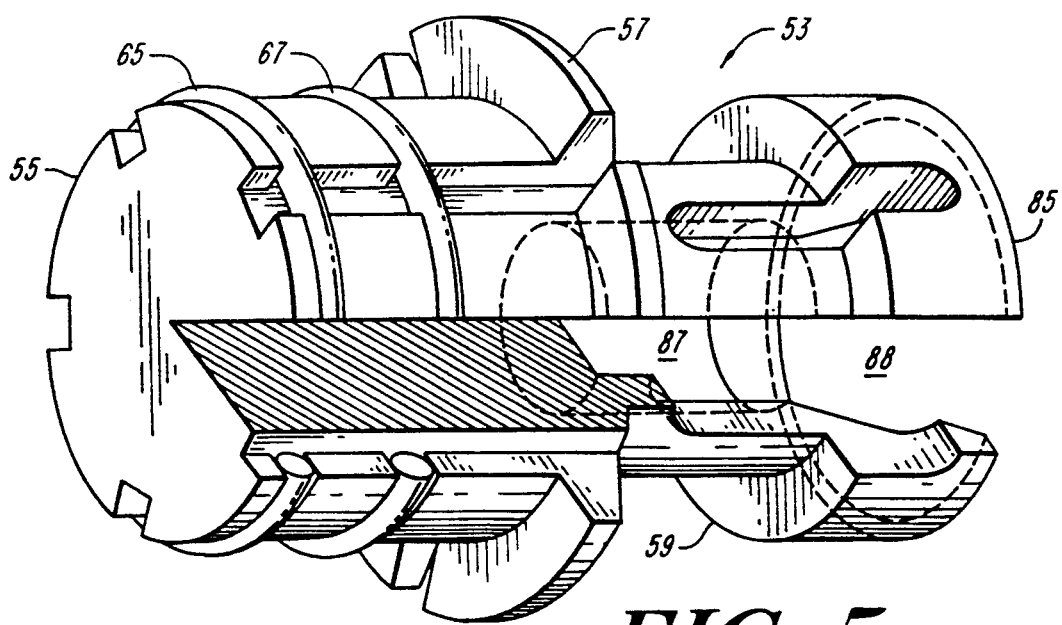
FIG. 5 is an orthogonal view of the adapter of FIGS. 3 and 4 which includes a partial sectional view of the adapter.
Figure 7:
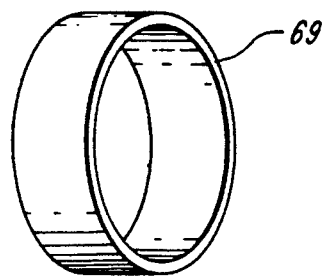
FIG. 7 is an orthogonal view of an annular member that can be utilized with the adapter of FIGS. 3-6 according to another embodiment of the present invention.
Figure 8:
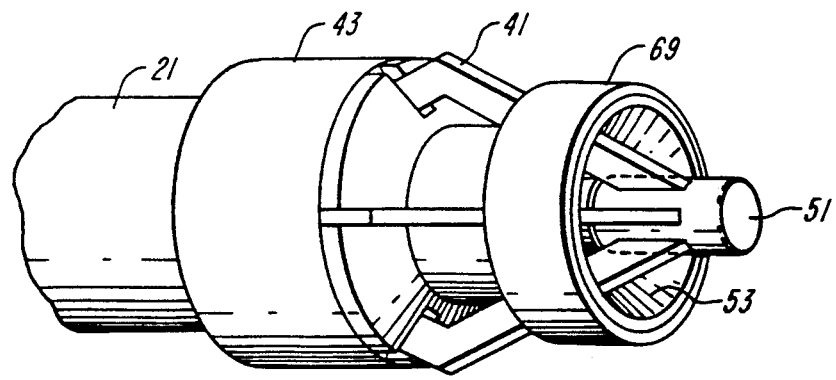
FIG. 8 is a view similar to that of FIG. 6 but showing the annular member of FIG. 7 installed on the adapter shown therein.
Figure 9:
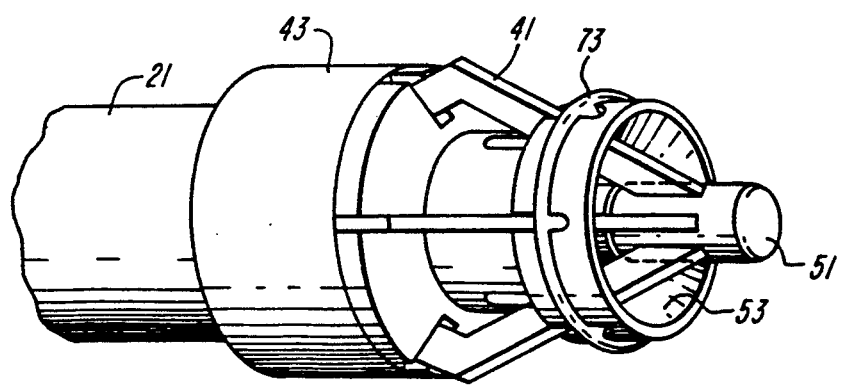
FIG. 9 is a view similar to that of FIG. 6 but showing still another embodiment of an adapter according to the present invention.

Referring now to the drawings, wherein like reference characters designate like or corresponding parts throughout the several views, there is shown in FIGS. 3-5 an adapter 53 including an engaging or retainable portion 55, a stopping or restricting portion 57, and a catching or receiving portion 59. Engaging portion 55 is provided with two parallel circumferential grooves 61 and 63 for respectively accommodating O-rings 65 and 67. O-rings 65 and 67 enable improved retention of engaging portion 55 within the hollow portion 44 of inner piston 42 of FIG. 2, while still permitting the engaging portion to slide within the hollow. Catching portion 59 is preferably provided with an annular member 69, as shown in FIGS. 7 and 8, to limit spreading of fingers 41, as is further discussed below. Annular member 69 can for example be press-fitted on catching portion 59. Alternatively, as shown in FIG. 9, the exterior of catching portion 59 can be provided with a groove for an O-ring 73 for the same purpose. As yet another alternative, tape such as electrical tape can be wrapped about and around the lower exterior portion of catching portion 59 for the same purpose. However, the groove and O-ring 73 are preferred for this purpose.

Figure 10:
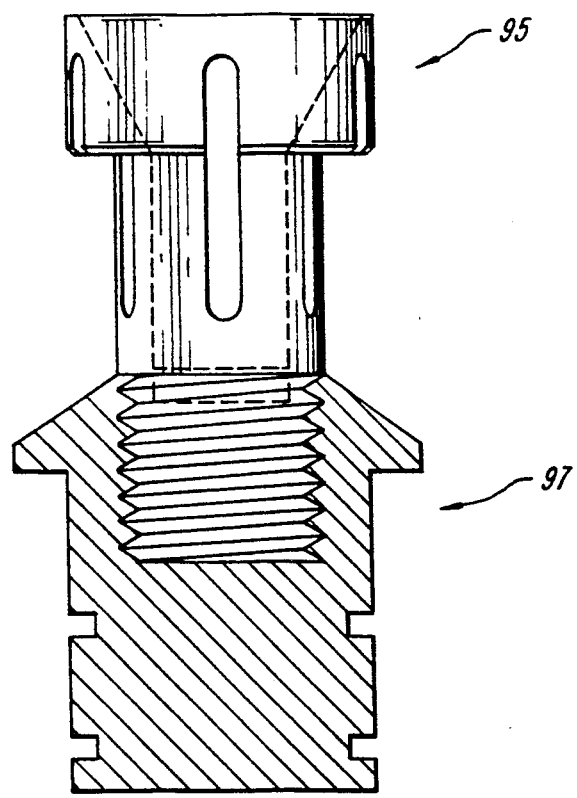
FIG. 10 shows a side elevation of yet another embodiment of the present invention with a portion shown in a sectional view.

The adapter can be formed of two pieces of material 95 and 97 as shown in FIG. 10. Alternatively, engaging portion 55, stopping portion 57 and catching portion 59 can each be separately formed and thereafter connected together. However, it is preferred, for easier manufacture, to construct the adapter from a single member or a single piece of material. Adapter 53 is preferably made of a hard plastic such as DELRIN TM or TORLON TM. Non-magnetic metals, such as aluminum and brass, could also be used but the magnet of chamber 13 could interfere if magnetic metals are used. The key requirements for the material for adapter 53 is that it be easily machined and mechanically durable.

Figure 6:
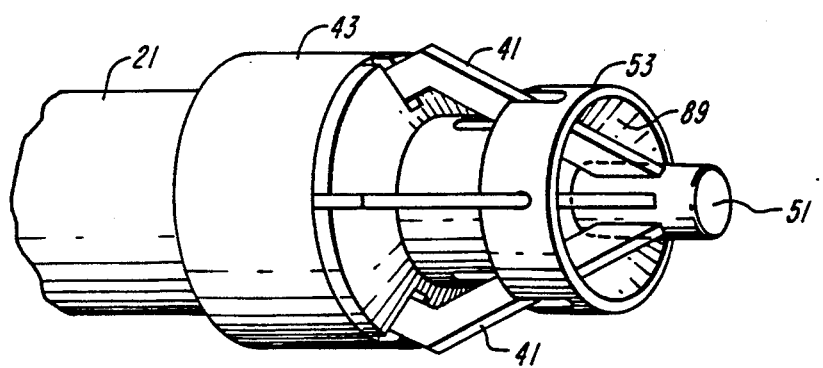
FIG. 6 shows an enlarged view of a portion of the apparatus of FIG. 1, which view corresponds to that of FIG. 2, but showing the adapter of FIGS. 3-5 installed thereon and the holder of FIG. 2A engaged thereby.

As shown in FIGS. 3-5, adapter 53 is provided with upper longitudinal grooves 83 and lower longitudinal slots 81. Grooves 83 and slots 81 are used to accommodate fingers 41, as shown in FIG. 6. On engaging portion 55, grooves 83 make it easier for the engaging portion, during insertion, to be moved past fingers 41 into hollow 44 of piston 42. Nonetheless, it is necessary to at least partially open or spread apart fingers 41 in order to pass engaging portion 55 therethrough. Although O-rings 65 and 67 obviously interfere with grooves 83, the grooves are less important in the upper portion of engaging portion 55 than in its lower region. However, grooves 83 are needed in stopping portion 57, and slots 81 are needed in catching portion 59, as shown in FIG. 6 to permit fingers 41 to continue to close properly without interference from adapter 53. A groove 83 and a slot 81 are accordingly provided in adapter 53 for each finger 41. Grooves 83 also make it relatively easy to remove adapter 53 from pincher 37 as desired; all that is required is to pull the adapter downwardly from the pincher.

As shown by broken lines in FIGS. 3-5 as well as solid lines in the sectional portion of FIG. 5, adapter 53 is provided with an interior cylindrical cavity 87 which communicates with the outside via slots 81, and via a chamfered opening 88 having its widest portion at the lower or distal end 85 of adapter 53 and catching portion 59. The interior end of cavity 87 is provided with some compatible plastic foam 93. Chamfer 89 provides a wider area for engagement of holder 51 when it is ejected from assembly 15, and its sloped surface helps guide the holder into cavity 87. Since the compressed air ejects holder 51 from chamber 13 with considerable force, due to the modifications made to chamber 13 to accommodate the holder, foam 93 is included at the interior and of cavity 87 to cushion the ejected holder and prevent damage thereto. Fingers 41 can engage and grasp holder 51 before it traverses the length of cavity 87, but in order to provide a longer response time for such engagement, it is preferred that such engagement take place after the holder has entered the cavity.

Adapter 53 of FIGS. 3-5 can for example be about 2½ inches long, with engaging portion 55 having an outer diameter of 1 inch, the widest part 75 of stopping portion 57 having a diameter of 1⅜ inch, and the wider or end portion 77 of catching portion 59 having a diameter of 1 inch. The longitudinal slots 81 and grooves 83, for five fingers 41, are preferably equally spaced at center to center intervals of 72°.

Another example of dimensions for adapter 53 of FIGS. 3-5 is given in this paragraph. Length of adapter 53 can be 61.1 mm. Engaging portion 55 can have a length of 25.0 mm, and an outer diameter of 24.8 mm, with grooves 61 and 63 being each 2.0 mm wide and separated by 8.0 mm. Stopping portion 57 can have a greatest outer diameter at 75 of 33.4 mm, with a 20° slope therefrom to catching portion 59. The narrower portion 79 of catching portion 5 can be 17.7 mm long. The distance from the open end 85 of catching portion 59 to the internal end of an upper longitudinal groove 83 can be 31.0 mm. The wider portion 77 of catching portion 59 can have an outer diameter of 25.0 mm, and an inner diameter of 21.0 mm at its open end. The narrower portion 79 of catching portion 59 can have a diameter of 17.0 mm. The internal cylindrical cavity 87 in catching portion 59 and stopping portion 57 can have a length of 31.0 mm and a diameter of 11.0 mm. The chamfer 89 between the cavity and the open end of catching portion 59 can have a 25° slope. The exterior of the internal end of the wider portion 77 of catching portion 59 can be provided with a 1.0 mm by 45° chamfer 91.

It is preferred that some restraining device be used with adapter 53 to prevent fingers 41 from spreading too far apart. This is preferred for three reasons. First, by keeping fingers 41 within adapter 53, the likelihood of damage to the rest of apparatus 17 or other structure during movement of pincher 37 is reduced or minimized. Second, by limiting the outward movement of fingers 41 beyond a point at which further such movement would be useless and unnecessary, there can be reduced expenditure of the pneumatic or other power source which controls the fingers. Third, with the fingers extended against such restraining device, they are disposed in slots 81 and cooperate with the interior chamfer 89 to help guide the ejected holder 51 into cavity 87.

One example of such a restraining device is a ring or collar 69 that is press-fitted on the wider portion 77 of catching portion 59. Alternatively, as shown in FIG. 9, the wider portion 77 can be provided with a circumferential groove to accommodate an O-ring 73; this is presently the best mode. As another alternative, the wider portion can be wrapped circumferentially with electrical tape or other tape.

It is of course undesirable that engaging portion 55 fall out of hollow 44, which O-rings 65 and 67 and fingers 41 help prevent. It is nonetheless desirable that engaging portion 55 be able to be moved within hollow 44. Such movement permits insertion and extraction of adapter 53. Accordingly, it is preferred that engaging portion 55 and/or hollow 44 be lightly covered with a vacuum grease or similar light lubricant.

Some of the many advantages of the present invention should now be readily apparent. For example, a novel adapter has been provided for a material handling apparatus that enables such apparatus to handle items differently sized from those which that apparatus was intended to handle. The adapter is capable of reducing damage to and loss of such differently sized items. The present adapter is furthermore capable of restricting extension of the fingers of that material handling apparatus to avoid damage to such apparatus and to other structure during movement of such fingers. The adapter enables such material handling apparatus to reliably grasp the differently sized items.

Obviously, many modifications and variations of the present invention are possible in light of the above teachings. It is therefore to be understood that the foregoing embodiments are presented by way of example only and that, within the scope of the appended claims and equivalents thereto, the invention may be practiced otherwise than as specifically described.

What is claimed is:

1. An adapter for a pick-up device having a plurality of members extending from an end of a hollow member, said adapter comprising:

a first portion for removable insertion into said hollow member, said first portion having a cross-sectional area no greater than that of the hollow member;

a stopping portion coupled to said first portion and having a cross-sectional area greater than that of the first portion, said stopping portion limiting insertion of said first portion into the hollow member; and a second portion coupled to said stopping portion, said second portion having a cavity substantially cylindrical in shape at a proximal end near the stopping portion, and having a distal end opposite said stopping portion, said cavity expanding from the cylindrical portion to said distal end, said second portion and said stopping portion each having openings for accommodating the plurality of members.

2. An adapter as recited in claim 1, further comprising cushioning means, disposed at the proximal end of said cavity for cushioning objects entering said cavity.

3. An adapter as recited in claim 1, further comprising restraining means, releasably disposed on at least a portion of said second portion, for restraining movement of the members away from said adapter.

4. An adapter as recited in claim 3 wherein:
said second portion is provided with an external groove about its perimeter; and
said restraining means comprises an O-ring disposed in said external groove.

5. An adapter as recited in claim 3 wherein said restraining means comprises an annular member disposed about and engaging at least a portion of said second portion.

6. An adapter as defined in claim 1 wherein the cavity extends from the cylindrical portion to the distal end via a chamfer.

7. An adapter as defined in claim 1 wherein the first and second portions are substantially cylindrical; wherein the openings in said stopping portion are grooves; and wherein said first, stopping, and second portions are symmetrical about a common longitudinal axis.

8. An adapter as defined in claim 7 further comprising a restraining means coupled to the second portion for limiting movement of said members away from said adapter.

9. Apparatus for releasable engagement and transport of an object comprising:
a pick-up device having a plurality of members extending from an end of a hollow member;
a first portion for removable insertion into said hollow member, said first portion having a cross-sectional area no greater than that of the hollow member;
a stopping portion coupled to said first portion and having a cross-sectional area greater than the area of the first portion for limiting insertion of said first portion into said hollow member; and
a second portion coupled to said stopping portion, said second portion having a cavity substantially cylindrical in shape at a proximal end near said stopping portion, and having a distal end opposite said stopping portion, said cavity expanding from the cylindrical portion to said distal end, said second portion and said stopping portion being provided with a plurality of openings for accommodating said plurality of members.

10. An adapter for a pick-up device for an object, the pick-up device having a plurality of members extending from an end of a hollow member, said adapter comprising:
retainable means for being slidably and releasably retained within said hollow member;
stopping means connected to said retainable means for contacting the end of said hollow member to limit movement of said retainable means into said hollow member; and
receptacle means connected to said stopping means, said receptacle means having an internal cavity substantially cylindrical in shape, and having a free end opposite said stopping means, said cavity extending to said free end via a chamfer expanding from said cavity to said free end for receiving the object, said receptacle means having a plurality of openings for accommodating the plurality of members.

11. An adapter as recited in claim 10, further comprising cushioning means, disposed in said cavity opposite said free end, for cushioning any object entering said cavity.

12. An adapter as recited in claim 10, further comprising restraining means, releasably disposed on at least a portion of said receptacle means, for restraining movement of the members away from said adapter.

* * * * *